(12) United States Patent
Sanghvi et al.

(10) Patent No.: US 6,677,120 B2
(45) Date of Patent: Jan. 13, 2004

(54) BUILDING BLOCKS FOR THE SOLUTION PHASE SYNTHESIS OF OLIGONUCLEOTIDES

(75) Inventors: Yogesh S. Sanghvi, Encinitas, CA (US); Vicente Gotor, Oviedo (ES); Miguel Ferrero, Oviedo (ES); Susana Fernandez, Oviedo (ES); Javier Garcia, Colunga (ES)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/822,903

(22) Filed: Mar. 30, 2001

(65) Prior Publication Data

US 2002/0142307 A1 Oct. 3, 2002

(51) Int. Cl.$^7$ ............................ C12Q 1/68; C12P 19/34; C07H 21/02; C07H 21/04; C07H 19/00
(52) U.S. Cl. ............................ 435/6; 435/7.1; 435/91.1; 435/91.2; 536/22.1; 536/23.1; 536/24.3; 536/24.31; 536/24.32; 536/24.33
(58) Field of Search ........................ 435/6, 7.1, 91.1, 435/91.2; 536/22.1, 23.1, 24.3–24.33

(56) References Cited

U.S. PATENT DOCUMENTS

| | | | |
|---|---|---|---|
| 4,474,947 A | 10/1984 | Hudson et al. | 536/27 |
| 5,538,891 A | 7/1996 | Schneider et al. | 435/280 |
| 5,594,117 A | 1/1997 | Udrea et al. | 536/23.1 |
| 6,222,030 B1 | 4/2001 | Dellinger et al. | 536/25.3 |

FOREIGN PATENT DOCUMENTS

WO    WO 00/66605 A2    11/2000

OTHER PUBLICATIONS

Uemura et al Tetrahedron Letters vol. 30 No. 29 pp. 3819–3820 1989.*

Copy of PCT Written Opinion dated May 19, 2003 (PCT/US02/08547).

Bornscheuer et al., *Hydrolases in Organic Synthesis. Regio– and Stereoselective Biotransformations*; Wily–VCH: Weinheim, 1999.

Carrea et al., "Properties and Synthetic Applications of Enzymes in Organic Solvents", *Angew. Chem. Int. Ed.*, 2000, 39, 2226–2254.

Ferrero et al., "Chemoenzymatic Transformations in Nucleoside Chemistry", *Monatsh. Chem.*, 2000, 131, 585–616.

Ferrero et al., "Biocatalytic Selective Modifications of Conventional Nucleosides, Carbocyclic Nucleosides, and C–Nucleosides", *Chem Rev.*, 2000, 100, 4319–4347.

Gotor et al., "Regioselective Acylation of 2'–Deoxynucleosides Through an Enzymatic Reaction with Oxime Esters", *Synthesis*, 1992, 626–628.

Iwai et al., "Large Scale Synthesis of Oligoribonucleotides on a Solid Support: Synthesis of a Catalytic RNA Duplex", *Tetrahedron*, 1990, 46, 6673–6688.

Iwai et al., "5'–Levulinyl and 2'–Tetrahydrofuranyl Protection for the Synthesis of Oligoribonucleotides by the Phosphoramidite Approach", *Nucleic Acids Res.*, 1988, 16, 9443–9456.

Moris et al., "A Useful and Versatile Procedure for the Acylation of Nucleosides Through an Enzymatic Reaction", *J. Org. Chem.*, 1993, 58, 653–660.

Reese et al., "The H–phosphonate Approach to the Solution Phase Synthesis of Linear and Cyclic Oligoribonucleotides" *Nucleic Acids Res.*, 1999, 27(4), 963–971.

Reese, C. B. et al., "The H–phosphonate Approach to the Synthesis of Oligonucleotides and Their Phosphorothioate Analogues in Solution," Perkin, *J. Chem. Soc. Perkin Trans.*, 1999, 1, 1477–1486.

* cited by examiner

*Primary Examiner*—Jeffrey Siew
(74) *Attorney, Agent, or Firm*—Woodstock Washburn LLP

(57) ABSTRACT

The present invention is directed to methods for the preparation of 3'-O and 5'-O-levulinyl nucleosides from common precursors using an enzymatic approach.

24 Claims, 4 Drawing Sheets a, B= T; b, B= C; c, B= C$^{Bz}$; d, B= A; e, B= A$^{Bz}$; f, B= G; g, B= G$^{iBu}$

Method A: LevOH, DCC, DMAP, Et$_3$N, 1,4-Dioxane.

Method B: LevOH, PS-carbodiimide, DMAP, DMAP·HCl, Et$_3$N, 1,4-Dioxane.

PS-carbodiimide

*PSL-C was used for di-Lev-dG$^{iBu}$ (2g) since CAL-A did not catalyze the hydrolysis.

a, B= A; R=Me
b, B= A; R=MOE
c, B= 5-Me-C; R=Me
d, B= 5-Me-C; R=MOE (a) LevOH, DCC, Et$_3$N, DMAP, 1,4-dioxane.
(b) 0.15M KPi ( pH=7), 1,4-dioxane.

Table 1. Regioselective Enzymatic Hydrolysis of di-Levulinyl esters 2.

| | | | | | Yield (%)[a] | |
|---|---|---|---|---|---|---|
| entry | substrate | enzyme | T (°C) | t (h) | 3 | 4 |
| 1 | 2a | CAL-B[b] | 40 | 62 | 85 | |
| 2 | 2b | CAL-B | 30 | 62 | 84 | |
| 3 | 2d | CAL-B | 40 | 28 | 98 | |
| 4 | 2g | CAL-B[c] | 40 | 18 | 80 | |
| 5 | 2a | CAL-A[b] | 40 | 86 | | 70 |
| 6 | 2c | CAL-A[b] | 40 | 62 | | 78 |
| 7 | 2e | CAL-A | 40 | 68 | | 85 |
| 8 | 2g | PSL-C | 60 | 28 | | 93 |

[a] Isolated yield.

[b] An extra fraction of lipase (30 mg) was added after 30 h.

[c] It was used a ratio of 1:2 w/w (2g/CAL-B).

a, B= T; b, B= C; c, B= $C^{Bz}$; d, B= A; e, B= $A^{Bz}$; f, B= G; g, B= $G^{iBu}$

FIGURE 4

BUILDING BLOCKS FOR THE SOLUTION PHASE SYNTHESIS OF OLIGONUCLEOTIDES

FIELD OF THE INVENTION

The present invention relates to methods for the preparation of 3'-O and 5'-O-levulinyl nucleosides from common precursors using an enzymatic approach. These methods are useful for the large-scale synthesis of oligonucleotides.

BACKGROUND OF THE INVENTION

It is well known that most of the bodily states in mammals, including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities.

Three principal methods have been used for the synthesis of oligonucleotides. The phosphotriester method, as described by Reese, *Tetrahedron* 1978, 34, 3143; the phosphoramidite method, as described by Beauage, in *Methods in Molecular Biology: Protocols for Oligonucleotides and Analogs*; Agrawal, ed.; Humana Press: Totowa, 1993, Vol. 20, 33–61; and the H-phosphonate method, as described by Froehler in *Methods in Molecular Biology: Protocols for Oligonucleotides and Analogs* Agrawal, ed.; Humana Press: Totowa, 1993, Vol. 20, 63–80.

The phosphotriester approach has been widely used for solution phase synthesis, whereas the phosphoramidite and H-phophonate strategies have found application mainly in solid phase syntheses. Recently, Reese reported a new approach to the solution phase synthesis of oligonucleotides on H-phosphonate coupling. See, Reese et al. *Nucleic Acids Research*, 1999, 27, 963–971, and Reese et al. *Biorg. Med. Chem. Lett.* 1997, 7, 2787–2792, which is incorporated herein by reference. Solution phase synthesis is the method of choice in producing large-scale quantities of oligonucleotides.

These solution phase methods require the use of nucleoside monomer building blocks bearing protecting groups on the 3'-O and/or the 5'-O positions. The protecting groups should be stable to coupling conditions and selectively cleaved without affecting other protecting groups in the molecule. One such protecting group is the levulinyl group, —C(O)—(CH$_2$)$_2$—C(O)—CH$_3$. However, the preparation of nucleosides bearing these protecting groups involves several tedious chemical protection/deprotection and/or purification steps.

For example, the 3',5'-di-O-levulinyl protection of nucleosides can be accomplished using a well-established method wherein nucleosides are selectively acylated at their hydroxyl sites by reacting the nucleosides with levulinic acid in the presence of DCC (dicyclohexylcarbodiimide). Despite the utility of this method, it suffers from at least one significant problem. The method requires a large excess of DCC to achieve optimal yields. The excess DCC is converted to DCU (dicyclohexylcarbodiimide) upon completion of the reaction, which must be separated from the reaction mixture. Unfortunately, for large-scale syntheses, the separation step requires considerable time and expense.

Prior to the present invention, synthesis of 5'-O-levulinyl nucleosides was accomplished by reacting parent nucleosides with levulinic acid and 2-chloro-1-methylpyridinium iodide. Iwai et al., *Nucleic Acids Res.* 1988, 16, 9443–9456; Iwai et al. *Tetrahedron* 1990, 46, 6673–6688. However, because this method does not afford selective acyaltion of the 5'-hydroxyl function, additional purification and deprotection steps are necessary because both 3'-acyl and 3',5'-diacyl derivatives are formed in the reaction. After the 3',5'-diacyl derivatives are separated by chromatography, the residue must be treated with DMTrCl to remove the 3'-acyl compound. Finally, an additional purification by chromatography isolates the 5'-O-levulinyl derivatives in very low yields.

Before now, the synthesis of 3'-O-levulinyl nucleosides (2'-deoxy or 2'-protected) was accomplished by the treatment of parent nucleosides with levulinic acid or levulinic anhydride and DCC. One of the major drawbacks of this method is that it requires that the 5'-hydroxyl function be protected as a 5'-O-DMTr group prior to acylation with levulinic acid. The 5'-O-DMTr group must then be removed in an acid medium to afford the 3'-O- protected nucleosides. See, Reese et al., *Nucleic Acids Res.* 1999, 27, 963–971, and Reese et al., *J. Chem. Soc., Perkin Trans.* 1 1999, 1477–1486.

Commercially viable methods for the large-scale synthesis of oligonucleotides are constantly being explored. It has been found that the application of biocatalysts in organic synthesis has become an attractive alternative to conventional chemical methods. See, Carrea, et al. *Angew. Chem. Int. Ed.* 2000, 39, 2226–2254; Bornscheuer, et al. *Hydrolases in Organic Synthesis. Regio- and Stereoselective Biotransformations*; Wiley-VCH: Weinheim, 1999. Enzymes catalyze reactions with high chemo-, regio-, and stereoselectivity. See, Ferrero et al. *Chem. Rev.* 2000, 100, 4319–4347; Ferrero et al., *Monatsh. Chem.* 2000, 131, 585–616. It has previously been reported that *Candida antarctica* lipase B (CAL-B) catalyzes acylation at the 5'-hydroxyl group of nucleosides with high selectivity. *Pseudomonas cepacia* lipase (PSL) shows unusual regioselectivity towards the secondary alcohol at the 3'-position of 2'-deoxynucleosides. Moris et al., *J. Org. Chem.* 1993, 58, 653–660; Gotor et al. *Synthesis* 1992, 626–628.

In the last few years the use of antisense oligonucleotides has emerged as an exciting new therapeutic paradigm. As a result, very large quantities of therapeutically useful oligonucleotides are required in the near future. In view of the considerable expense and time required for synthesis of oligonucleotide building blocks, there has been a longstanding effort to develop successful methodologies for the preparation of oligonucleotides with increased efficiency and product purity.

SUMMARY OF THE INVENTION

Applicants have discovered methods that are useful in, for example, the large-scale synthesis of oligonucleotides. The methods of the present invention help to minimize the number of steps required to yield desired results using an enzymatic approach. Applicants have found that both 3'-O-levulinyl nucleosides and 5'-O-levulinyl nucleosides can be prepared from a common precursor the regioselective deprotection of a 3', 5'-di-O-levulinyl nucleoside to yield the desired 3'-O-levulinyl nucleoside or 5'-O-levulinyl nucleoside. Surprisingly, it has been found that the presence of selected lipases in deprotection reaction protocols gives rise to regioselectivity of deprotection According to one embodiment, a method is provided for regioselectively deprotecting a 3',5'-di-O-levulinylnucleoside comprising selecting a lipase that is effective to direct a regioselective hydrolysis of one of the levulinyl positions, without causing an undesired level of hydrolysis on the other of the levulinyl positions, and contacting the 3',5'-di-O-levulinyl nucleoside with the lipase for a time and under conditions effective to yield either a 3'-O-levulinyl or a 5'-O-levulinyl nucleoside. Examples of lipases that are amenable to the present invention include *Candida antarctica* lipase B (CAL-B), *Candida antarctica* lipase A (CAL-A), *Pseudomonas cepacia* lipase (PSL), porcine pancreatic lipase, *Chromobacteriaum viscosum* lipase, *Mucor miehei* lipase, *Humicola lanuginosa* lipase, *Penicillium camemberti* lipase, *Candida rugosa* lipase, and others.

According to an embodiment of the present invention, a 3',5'-di-O-levulinyl nucleoside is deprotected at the 5'-O-levulinyl position by contacting the diprotected nucleoside with CAL-B for a time and under conditions effective to regioselectively hydrolyze the 5'-O-levulinyl position without affecting the 3'-O-levulinyl position.

In another embodiment, a 3'-, 5'-di-O-levulinyl nucleoside is deprotected at the 3'-O levulinyl position by contacting the diprotected nucleoside with CAL-A or PSL-C for a time and under conditions effective to regioselectively hydrolyze the 3'-O-levulinyl position without affecting the 5'-O-levulinyl position.

In some embodiments of the present invention, methods are disclosed for regioselectively deprotecting a 3'-, 5'-di-O-levulinyl nucleoside at the 5'-O-levulinyl position wherein the nucleoside has one of the following formulas:

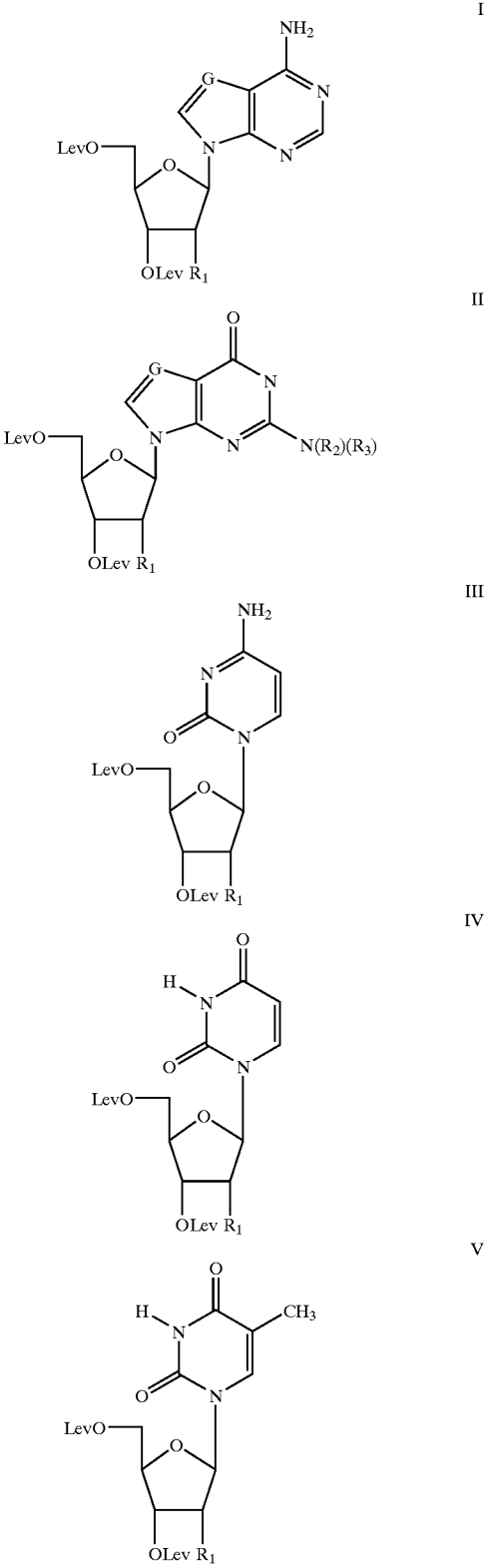

wherein:
$R_1$ is —H, -hydroxyl, a protected hydroxyl, a 2'-substituent or a 2'-protected substituent; and
$R_2$ and $R_3$ are, independently, —H or an amino protecting group;

G is N or CH; and

Lev is —C(O)—(CH$_2$)$_2$—C(O)—CH$_3$, the levulinyl group;

comprising selecting a lipase that is effective to direct a regioselective hydrolysis of the 5'-O-levulinyl position, without causing hydrolysis on the 3'-O-levulinyl position, and contacting the 3',5'-di-O-levulinyl nucleoside with the lipase for a time and under conditions effective to yield a 3'-O-levulinyl nucleoside. A preferred lipase for 5'-O-levulinyl hydrolysis is CAL-B.

In still further embodiments, methods are provided for regioselectively deprotecting a nucleoside at the 3'-O-levulinyl position wherein the nucleoside has one of the following formulas:

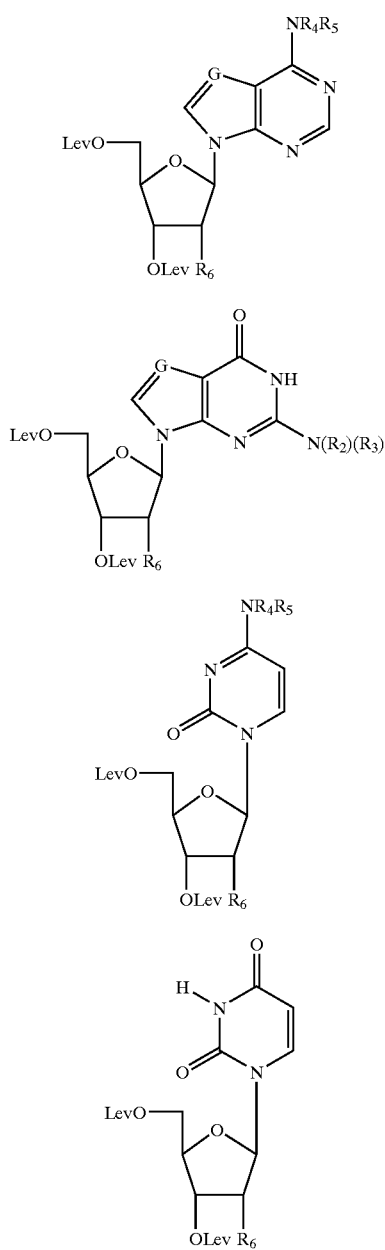

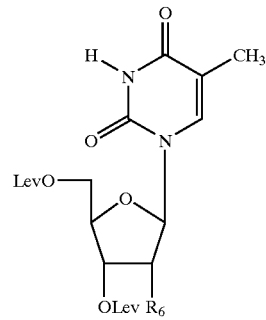

wherein:

R$_6$ is —H, -hydroxyl;

R$_2$, R$_3$, R$_4$, and R$_5$ are each, independently, —H or an amino protecting group;

G is N or CH; and

Lev is —C(O)—(CH$_2$)$_2$—C(O)—CH$_3$;

comprising selecting a lipase that is effective to direct a regioselective hydrolysis of the 3'-O-levulinyl position, without causing hydrolysis of the 5'-O-levulinyl position, and contacting the 3',5'-di-O-levulinyl nucleoside with the lipase for a time and under conditions effective to yield a 5'O-levulinyl nucleoside. Lipases that are preferable for hydrolysis at the 3'-O-levulinyl positions are, for example, CAL-A or PSL-C.

In some embodiments of the present invention, methods for acylating a hydroxyl moiety of a nucleic acid, such as a nucleoside or a nucleotide, at at least one of a 2'-O, 3'-O, or 5'-O position are provided comprising reacting the nucleic acid with levulinic acid in the presence of a coupling agent, such as a carbodiimide, that is attached to a polymeric support for a time and under conditions effective to form an ester at the 2'-O, 3'-O or 5'-O position. Preferred polymeric supports comprise polystyrene or polyethylene glycol polymeric supports that are attached to cyclohexylcarbodiimide.

The present invention includes the esterification or acylation of any hydroxyl moiety, such as those found in carbohydrates or steroid molecules, by reacting the compounds containing the hydroxyl moiety with levulinic acid in the presence of a coupling agent that is attached to a polymeric support for a time and under conditions effective to form an ester between the hydroxyl moieties and the levulinyl group of the levulinic acid. In some embodiments of the present invention, methods are provided for acylating at least one hydroxyl moiety on a compound having the following formula:

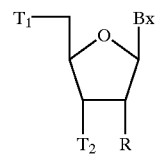

wherein:

B$_x$ is a nucleobase;

T$_1$ and T$_2$ are, independently, -hydroxyl, a hydroxyl protecting group, an activated phosphate group, a nucleotide, a nucleoside, or an oligonucleotide;

R is —H, -hydroxyl, a protected hydroxyl or a 2' substituent group;

provided that at least one of $T_1$, $T_2$ or R is -hydroxyl; comprising reacting the compound with levulinic acid in the presence of a coupling agent that is attached to a solid support, such as PS-cyclohexylcarbodiimide, for a time and under conditions effective to form an ester between the hydroxyl moiety and the levulinyl group. In a preferred embodiment, $T_1$ and $T_2$ are —OH and R is —H or a 2'-substituent.

In one preferred embodiment, methods are provided for acylating the 3'-O and 5'-O positions of a compound having the following formula:

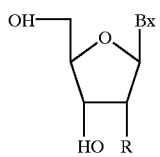

wherein:

$B_x$ is a nucleobase; and

R is hydroxyl or an optionally protected 2'-substituent comprising reacting the compound with levulinic acid in the presence of a coupling agent that is attached to a solid support for a time and under conditions effective to form a compound having formula:

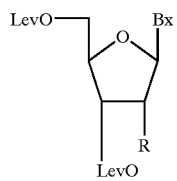

wherein Lev is -levulinyl.

According to one embodiment of the present invention, methods are provided for generating a cyclohexylcarbodiimide derivatized polymeric support from a cyclohexylurea derivatized polymeric support comprising reacting the cyclohexylurea derivatized polymeric support with a dehydrating agent, such as tosyl chloride or $POCl_3$, in an organic solvent for a time and under conditions effective to yield the cyclohexylcarbodiimide derivatized polymeric support. In some embodiments, the organic solvent employed is $CH_2Cl_2$, $CHCl_3$, hexane, or pyridine.

In a further embodiment of the present invention, a method is provided for generating a cyclohexylcarbodiimide derivatized polymeric support from a cyclohexylurea derivatized polymeric support comprising the steps of reacting the cyclohexylurea derivatized polymer support with a dehydrating agent for a time and under conditions effective to form a salt and subsequently contacting the salt with an aqueous solution, such as aqueous NaOH, to form the cyclohexylcarbodiimide derivatized polymeric support.

BRIEF DESCRIPTION OF THE DRAWINGS

The numerous objects and advantages of the present invention may be better understood by those skilled in the art by reference to the accompanying detailed description and the following drawings, in which:

FIG. 4 is a table depicting the results of regioselective hydrolysis of nucleosides 2a–2g.

The present invention is directed to the preparation of nucleoside building blocks such as 3',5'-di-O-levulinylnucleosides, 3'-O-levulinylnucleosides, and 5'-O-levulinylnucleosides that are especially useful in the large-scale synthesis of oligonucleotides.

According to one embodiment of the present invention, a method is provided for protecting a hydroxyl moiety of a nucleic acid at at least one of a 2'-O, 3'-O, or 5'-O position comprising reacting the nucleic acid with levulinic acid in the presence of a coupling agent that is attached to a polymeric support for a time and under conditions effective to form an ester at the 2'-O, 3'-O or 5'-O position. The nucleic acids of the present invention include nucleosides, nucleotides, oligonucleosides and oligonucleotides. In some embodiments, the nucleic acid is a nucleoside and the polymeric support is a polystyrene support or a polyethylene glycol support that is coupled to a coupling agent, such as cyclohexylcarbodiimide.

In a preferred embodiment, the nucleic acid has the formula:

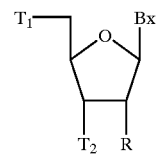

wherein:

$B_x$ is a nucleobase;

$T_1$ and $T_2$ are, independently, hydroxyl, a protected hydroxyl, an activated phosphate group, a nucleotide, a nucleoside, or an oligonucleotide; and R is —H, -hydroxyl, a protected hydroxyl, or a 2' substituent group;

provided that at least one of $T_1$, $T_2$ or R is —OH;

comprising reacting the compound with levulinic acid in the presence of a coupling agent that is attached to a solid support for a time and under conditions effective to form an ester between the hydroxyl moiety and the levulinyl group. In a preferred embodiment, $T_1$ and $T_2$ are —OH and R is H.

The protection methods of the present invention are not limited to acylation of the hydroxyl groups of nucleosides. Any hydroxyl functionality may be acylated using the methods of the present invention, including those found in carbohydrate or steroid molecules.

Figure 1:
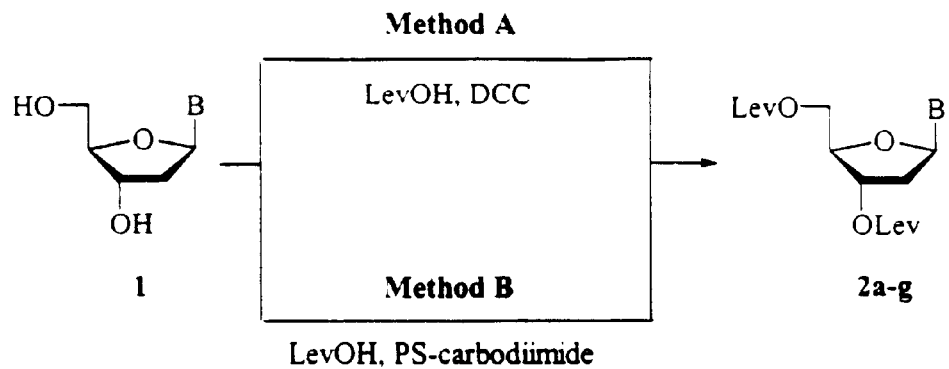
FIG. 1 shows 3',5'-di-O-acylation of a 2'-deoxynucleoside using levulinic acid and DCC or levulinic acid and PS-carbodiimide.
Figure 1:
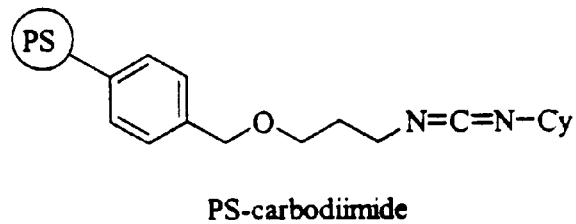
Figure 1:
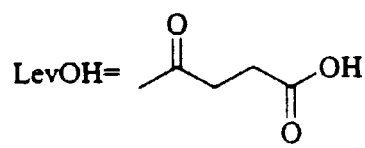

According to one method of the present invention, referring to FIG. 1, 3',5'-di-O-levulinyl nucleosides (2) were prepared from their corresponding natural nucleosides by treatment with levulinic acid and PS-carbodiimide in 1,4-dioxane in the presence of DMAP as a catalyst. Filtering off of the polystyrene beads removed the urea and the N-levulinylurea derivatives, which were polymer bound. 3',5'-di-O-levulinylthymidine (2a) and 3',5'-di-O-levulinyl-2'-deoxyadenosine (2d) were isolated with 91% and 95% yield, respectively. The PS-dicarbodiimide, an expensive reagent, is recovered by reacting the cyclohexylurea derivatized polymer support with a dehydrating agent in an organic solvent. Preferred dehydrating agents include $POCl_3$ and tosylchloride. Preferred organic solvents include $CH_2Cl_2$, $CHCl_3$, hexane, and pyridine.

Referring again to FIG. 1, 3',5'-di-O-levulinyl nucleosides can alternatively be prepared from the corresponding natural nucleosides (1) by treatment with 5.2 equivalents of levulinic acid (LevOH) and dicyclohexylcarbodiimide (DCC) in 1,4-dioxane in the presence of DMAP as catalyst. The reaction takes place through activation of the levulinic acid with DCC to obtain the O-acylurea intermediate. The excess of adduct evolves into the stable N-acylurea which was isolated like DCU as byproducts in the process. 3',5'-Dilevulinyl derivatives (2) were obtained in high yields (70–95%) after flash chromatography. The crude residue of the reactions was washed with Et$_2$O to eliminate the N-acylurea and subsequently dissolved in EtOAc from which the remaining DCU was separated by filtration. Almost quantitative yields were achieved for this acylation reaction. The level of purity was based on their $^1$H-NMR which showed just traces of DCU and N-levulinylurea. Under these conditions no acylation was observed in the amino group of 2'-deoxyadenosine (1d) and 2'-deoxyguanosine (1f). In the case of 2'-deoxycytidine (1b), less amount of LevOH and DCC (3 equivalents) were used to minimize the formation of the aminoacyl derivative. As a consequence, longer reaction times were needed and some amount of the starting material remained unchanged. In spite of that, 68% isolated yield of 3',5'-di-O-levulinyl-2'-deoxycytidine (2b) were obtained after flash chromatography.

Regioselective deprotection of the common precursor, 3',5'-di-O-levulinyl nucleoside, at the 5'-O-levulinyl position is effected by selecting a lipase effective to direct regioselective hydrolysis at the 5'-O-levulinyl position, without causing hydrolysis at the 3'-O-levulinyl position, and contacting the diprotected nucleoside with the lipase for a time and under conditions effective to hydrolyze the 3',5'-di-O-levulinyl nucleoside at the 5'-O-levulinyl position. In some embodiments, the diprotected nucleosides have one of the following formulas:

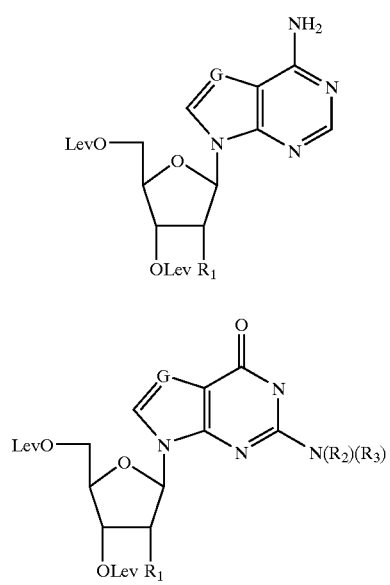

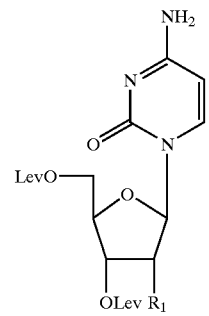

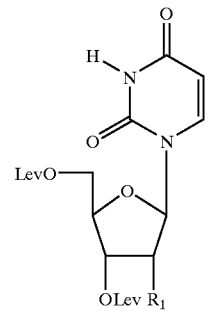

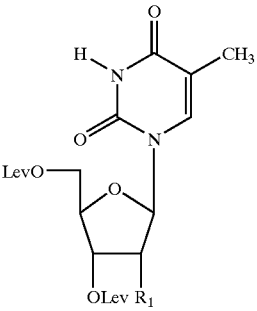

wherein:
R$_1$ is —H, -hydroxyl, a protected hydroxyl, or a 2'-substituent; and
R$_2$ and R$_3$ are, independently, —H or an amino protecting group;
G is N or CH; and
Lev is —C(O)—(CH$_2$)$_2$—C(O)—CH$_3$.

Figure 2:
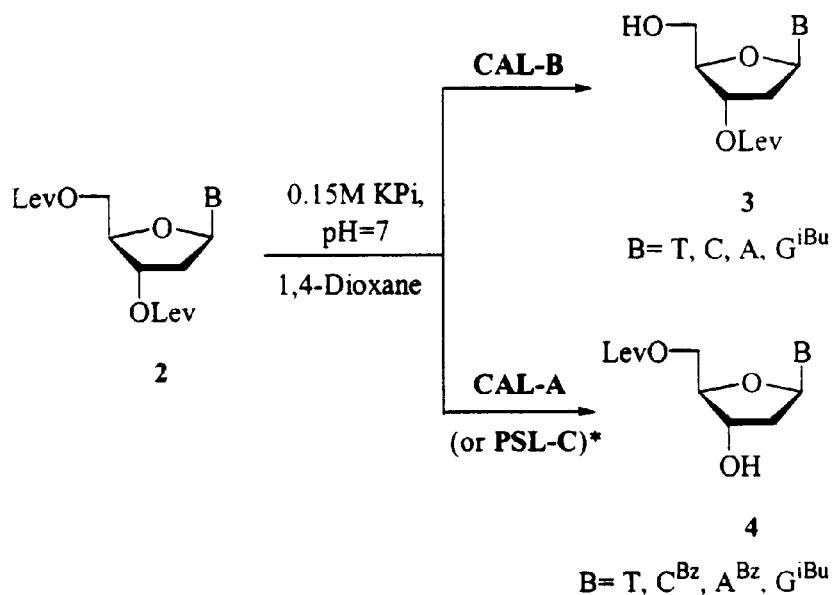
FIG. 2 shows the enzymatic regioselective hydrolysis of a 3',5'-di-O-levulinyl 2'-deoxynucleoside.

For example, referring to FIG. 2, a 3',5'-di-O-levulinylthymidine (2a) was treated with CAL-B at 40° C. in 0.15M phoshpate buffer (pH=7) containing 18% of 1,4-dioxane. TLC showed total disappearance of the starting material after 62 h (entry 1, Table 1). After usual workup, as described by Myers et al. *Trends Pharmacol. Sci.* 2000, 21, 19–23; Cook, *Nucleosides Nucleotides* 1999, 18, 1141–1162; Crooke, et al. *Annu. Rev. Pharmacol. Toxicol.* 1996, 36, 107–129; and Matteucci et al. 1996, 384, 20–22, the contents of which are all incorporated by reference herein. $^1$H-NMR spectra clearly indicated the selective hydrolysis of the 5'-levulinic ester and the presence of 3'-O-levulinylthymidine (3a) as unique product. Traces of thymidine formed in the enzymatic reaction (showed by TLC) remained in the aqueous phase after extraction. Thus, pure compound (3a) was isolated with 85% yield.

Table 1, shown in FIG. 4, also indicates that substrates 3',5'-di-O-levulinyl cytosine (2b), 3',5'-di-O-levulinyl adenosine (2d), and 3',5'-di-O-levulinyl-N-isobutylguanosine (2g) exhibit excellent selectivity towards the 5'-position, when hydrolyzed in the presence of CAL-B. The absence of the 5'-O-levulinyl derivative and the high yields with which the reactions take place are noteworthy. Also, in these cases, TLC showed traces of completely hydrolyzed nucleoside, which was easily removed with an aqueous extraction.

The hydrolysis reaction catalyzed by CAL-B on N-benzoyl-di-O-levulinyl-2'-deoxycytidine (2c) and N-benzoyl-di-O-levulinyl-2'-deoxyadenosine (2e) afforded N-benzoyl-2'-deoxycytidine (1c) and N-benzoyl-2'-deoxyadenosine (1e), respectively. Although several reaction conditions were tried, the process takes place without regioselectivity. It seems that the active site of CAL-B did not accommodate the N-protected adenosine and cytosine in the same manner as their unprotected counterparts. While not wishing to be bound to any particular theory, it is possible that the phenyl group could have some steric contact within the binding site, which may lead to unfavorable results.

Figure 3:
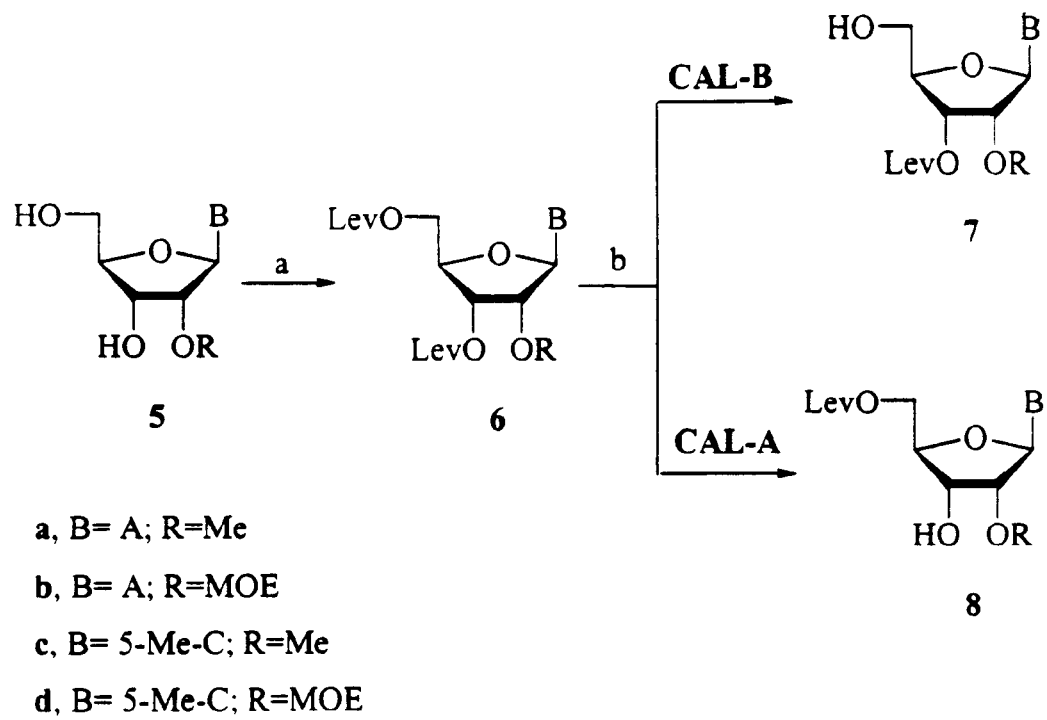
FIG. 3 shows the enzymatic regioselective hydrolyis of a 3',5'-di-O-levulinyl 2'-substituted nucleoside.

2'-substituted nucleosides are also successfully selectively deprotected at the 5'-O-levulinyl position. Referring to FIG. 3, all four nucleosides, 2'-methoxy-3',5'-di-O-levulinyladenosine (6a), 2'-methoxyethoxy-3',5'-di-O-levulinyladenosine (6b), 2'methoxy-3',5'-di-O-levulinyl-2'-deoxycytosine (6c), and 2'-methoxyethoxy-3',5'-di-O-levulinyl-5-methyl cytosine (6d) were selectively hydrolyzed with CAL-B furnishing 7a–7d in high yields. The times and conditions effective to hydrolyze the nucleosides are not limited to those exemplified herein. Various times and conditions are effective to hydrolyze the esters, which will be recognized by those of skill in the art.

In one embodiment of the present invention, 3',5'-di-O-levulinyl nucleosides are regioselectively deprotected at the 3'-O-levulinyl position by selecting a lipase effective to direct regioselective hydrolysis at the 3'-O-levulinyl position, without causing hydrolysis at the 5'-O-levulinyl position, and contacting the diprotected nucleoside with the lipase for a time and under conditions effective to hydrolyze the 3',5'-di-O-levulinyl nucleoside at the 3'-O-levulinyl position. In some embodiments, the diprotected nucleosides have one of the following formulas:

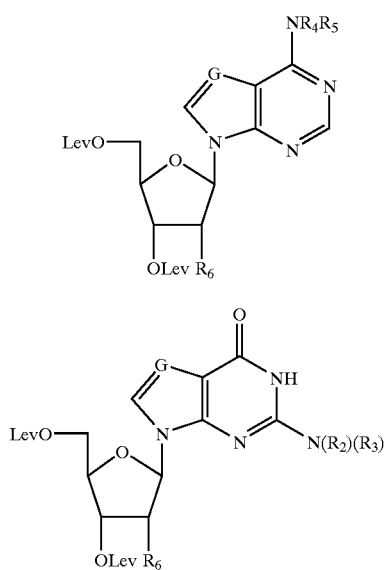

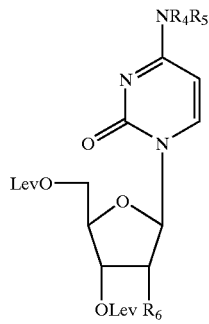

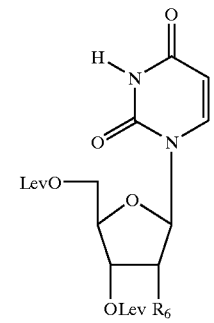

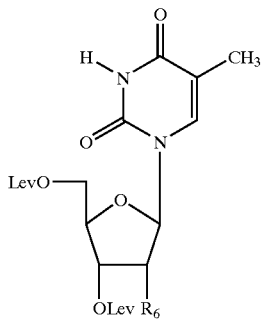

wherein:
$R_6$ is —H, or —OH;
$R_2$, $R_3$, $R_4$, and $R_5$ are each, independently, —H or an amino protecting group;
G is N or CH; and
Lev is —C(O)—(CH$_2$)$_2$—C(O)—CH$_3$.

For example, referring to FIG. 2, 3'-O- selective hydrolysis was accomplished by reaction of 2 with immobilized *Pseudomonas cepacia* lipase [PSL-C, ratio of 1:3 w/w (2/PSL-C)] at 60° C. in 0.15M phosphate buffer giving the 5'-O-levulinyl derivative. *Candida antarctica* lipase A (CAL-A) also exhibited excellent selectivity towards the 3'-O-levulinyl position and has the advantage of requiring lower reaction temperatures than PSL-C (40° C. instead of 60° C.), shorter reaction times, and a lower ratio of enzyme/starting material (see FIG. 4). Thus, 5'-O-levulinylthymidine (4a), N-benzoyl-5'-O-levulinyl-2'-deoxycytidine (4c), and N-benzoyl-5'-O-levulinyl-2'-deoxyadenosine (4e) were obtained with high yields (70–85%). The 3'-levulinyl regioisomer was not detected by TLC or $^1$H-NMR of the crude reaction mixture. TLC showed traces of parent nucleosides 1.

N-isobutyryl-3',5'-di-O-levulinyl-2'-deoxyguanosine (2g) was not selectively hydrolyzed with CAL-A. However, treatment with PSL-C afforded the N-isobutyryl-5'-O-levulinyl-2'-deoxyguanosine (4g), which was isolated after 28 h at 60° C. with 93% yield (entry 8, Table 1). N-Benzoyl-di-levulinyl derivatives (2c) and (2e) were both appropriate substrates for both lipases, PSL-C and CAL-A.

Treatment of 2'-OR nucleosides, as shown in FIG. 3 with PSL-C or CAL-A yielded a mixture of 3'-O-levulinyl and 5'-O-levulinyl nucleosides, without the selectivity that was demonstrated with unprotected 2'-O and 2'-deoxynucleosides. While not being bound to any particular theory, this may be the result of steric hindrance caused by the 2'-O—R group, making the 3'-O-levulinyl group inaccessible for selective hydrolysis by either of these lipases.

The nucleic acids of the present invention include naturally occurring and non-naturally occurring nucleosides and nucleotides. The nucleosides and nucleotides of the present invention are not limited to monomer units but may also contain a plurality of linked monomer units, to form dinucleosides, nucleotides, and oligonucleotides and comprise naturally and non-naturally occurring nucleobases, sugars, and backbones.

Non-naturally occurring nucleosides and nucleotides may be modified by replacing the sugar moiety with an alternative structure which has primary and secondary alcohol groups similar to those of ribose. Non-naturally occurring sugars and nucleosidic bases are typically structurally distinguishable from, yet functionally interchangeable with, naturally occurring sugars (e.g. ribose and deoxyribose) and nucleosidic bases (e.g., adenine, guanine, cytosine, thymine). Thus, non-naturally occurring nucleobases and sugars include all such structures which mimic the structure and/or function of naturally occurring species, and which aid in the binding of the oligonucleotide to a target, or which otherwise advantageously contribute to the properties of the oligonucleotide.

Backbone modifications include modifications to the phosphate backbone to increase the resistance to nucleases. These modifications include use of linkages such as methyl phosphonates, phosphorothioates and phosphorodithioates as well as those modifications that dramatically alter the nature of the internucleotide linkage such as non-phosphorus linkages, peptide nucleic acids (PNA's) and 2'-5' linkages.

A heterocyclic base moiety (often referred to in the art simply as a "base" or a "nucleobase") amenable to the present invention includes both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B., ed., CRC Press, 1993.

Certain heterocyclic base moieties are particularly useful for increasing the binding affinity of the oligomeric compounds of the invention to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,587, filed on Dec. 10, 1996, also herein incorporated by reference.

A representative list of 2'-substituent groups amenable to the present invention include $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alkylamino, O-alkylalkoxy, O-alkylaminoalkyl, O-alkyl imidazole, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen particularly fluoro), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula $(O-alkyl)_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional substituent groups amenable to the present invention include —SR and —$NR_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-$NR_2$ nucleosides are disclosed by Goettingen, M., *J. Org. Chem.*, 1996, 61, 73–6281; and Polushin et al., *Tetrahedron Lett.*, 1996, 37, 3227–3230.

Further substituent groups have one of formula I or II:

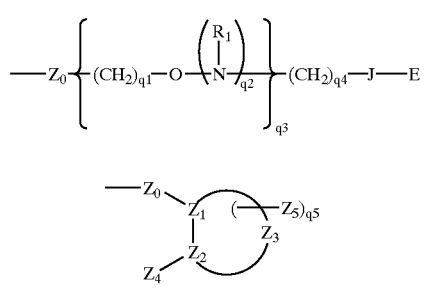

wherein:

$Z_0$ is O, S or NH;

J is a single bond, O or C(=O);

E is $C_1$–$C_{10}$alkyl, $N(R_1)(R_2)$, $N(R_1)(R_5)$, $N=C(R_1)(R_2)$, $N=C(R_1)(R_5)$ or has one of formula III or IV;

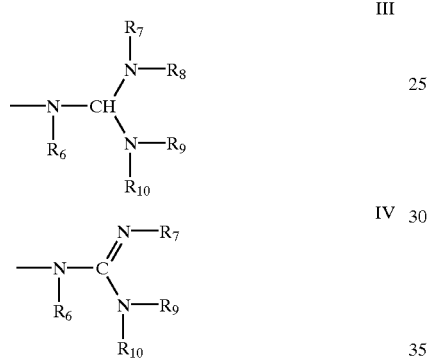

each $R_6$, $R_7$, $R_8$, $R_9$ and $R_{10}$ is, independently, hydrogen, $C(O)R_{11}$ substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_5$ is T—L,

T is a bond or a linking moiety;

L is a chemical functional group, a conjugate group or a solid support material;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_{3'}$, $N(R_3)(R_4)$, guanidino or acyl where said acyl is an acid amide or an ester;

or $R_1$ and $R_2$, together, are a nitrogen protecting group or are joined in a ring structure that optionally includes an additional heteroatom selected from N and O;

or $R_1$, T and L, together, are a chemical functional group;

each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, C(=NH)N(H)$R_5$, C(=O)N(H)$R_5$ or OC(=O)N(H)$R_5$;

$R_5$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$, or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

Representative substituent groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, now U.S. Pat. No. 6,271,358 filed Aug. 7, 2001 entitled "RNA Targeted 2'-Modified Oligonucleotides that are Conformationally Preorganized," hereby incorporated by reference in its entirety.

Particularly preferred substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, O(CH$_2$)$_n$ON[(CH$_2$)$_n$CH$_3$)]$_2$ (where n and m are from 1 to about 10), $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino and substituted silyl. Another particularly preferred modification includes 2'-methoxyethoxy (2'-O—CH$_2$CH$_2$OCH$_3$ or 2'-MOE, Martin et al., Helv. Chim. Acta, 1995, 78, 486). A further preferred substituent group is 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, also identified by attorney docket number ISIS-3993, entitled Aminooxy-Functionalized Oligomers and Methods for Making Same; hereby incorporated by reference in their entirety.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5'-position at a 5'-terminus. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531; 5,639,873; 5,646,265; 5,658,873; 5,670,633; and 5,700,920, certain of which are commonly owned, and each of which is herein incorporated by reference, and commonly owned U.S. Pat. No. 5,859,221, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. patent application Ser. No. 09/378,568, entitled "2'-O-Acetamido Modified Monomers and Oligomers", filed Aug. 19, 1999, also identified by attorney docket number ISIS-4071, hereby incorporated by reference in its entirety.

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, also identified by attorney docket number ISIS-4045, hereby incorporated by reference in its entirety.

The methods of the present invention use labile protecting groups to protect various functional moieties during synthesis. Protecting groups are used ubiquitously in standard oligonucleotide synthetic regimes for protection of several different types of functionality. In general, protecting groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. Representative protecting groups useful to protect nucleotides during synthesis include base labile protecting groups and acid labile protecting groups. Base labile protecting groups are used to protect the exocyclic amino groups of the heterocyclic nucleobases. This type of protection is generally achieved by acylation. Two commonly used acylating groups for this purpose are benzoylchloride and isobutyrylchloride. These protecting groups are stable to the reaction conditions used during oligonucleotide synthesis and are cleaved at approximately equal rates during the base treatment at the end of synthesis.

Hydroxyl protecting groups typically used in oligonucleotide synthesis may be represented by the group having the formula: —C(R$_1$)(R$_2$)(R$_3$) wherein each of R$_1$, R$_2$ and R$_3$ is an unsubstituted or mono-substituted aryl or heteroaryl group selected from phenyl, naphthyl, anthracyl, and five or six membered heterocylic rings with a single heteroatom selected from N, O and S, or two N heteroatoms, including quinolyl, furyl, and thienyl; where the substituent is selected from halo (i.e., F, Cl, Br, and I), nitro, C$_1$–C$_4$-alkyl or alkoxy, and aryl, aralkyl and cycloalkyl containing up to 10 carbon atoms; and wherein R$_2$ and R$_3$ may each also be C$_1$–C$_4$-alkyl or aralkyl or cycloalkyl containing up to 10 carbon atoms.

As will be recognized, additional objects, advantages, and novel features of this invention will become apparent to those skilled in the art upon examination of the following examples thereof, which are not intended to be limiting.

EXPERIMENTAL

General

Candida antarctica lipase B (CAL-B) was a gift from Novo Nordisk Co. Candida antarctica lipase A (CAL-A) and immobilized Pseudomonas cepacia lipase (PSL-C) were purchased from Roche Diagnostics S. L. and Amano Pharmaceuticals, respectively. PS-carbodiimide was purchased from Argonaut Technologies (San Carlos, Calif., EE.UU.). All other reagents were purchased from Aldrich or Fluka. Solvents were distilled over an adequate desiccant under nitrogen.

3',5'-di-O-Levulinyl-2'-deoxynucleosides (2)

Method A: To a stirred mixture of 1 (2 mmol) and Et$_3$N (1.7 mL, 12 mmol) in 1,4-dioxane (20 mL) under nitrogen, was added levulinic acid (1.21 g, 10.4 mmol), DCC (2.14 g, 10.4 mmol), and DMAP (20 mg, 0.16 mmol). The reaction was stirred at room temperature for 3 hours. In order to minimize the formation of triprotected cytidine derivative, 6 mmol both of LevOH and DCC, and 5 mmol of Et$_3$N were used for 1b. The insoluble material was collected by filtration and the filtrate was evaporated under vacuum. The residue was taken up in NaHCO$_3$ (aq) and extracted with CH$_2$Cl$_2$. The combined organic extracts were dried over Na$_2$SO$_4$ and evaporated. Cold Et$_2$O was added, and the slurry was scratched until crystallization occurs. The solid was filtered and washed with cold Et$_2$O, and then was poured in EtOAc (MeOH in case of 2f). The insoluble material was filtered and the filtrate was concentrated to afford the title compounds. The resulting materials were pure enough to be carried directly on to the enzymatic hydrolysis step. Further purification by flash chromatography (EtOAc) give pure 3',5'-di-O-levulinylnucleosides 2a–g.

Method B: To a stirred mixture of 1 (0.4 mmol) and Et$_3$N (0.15 mL, 1 mmol) in 1,4-dioxane (5 mL) under nitrogen, was added levulinic acid (0.14 g, 1.2 mmol), PS-carbodiimide (1.05 g, 1.2 mmol), DMAP (4 mg, 0.032 mmol), and DMAP.HCl (3 mg, 0.02 mmol). The reaction was stirred at room temperature for 3 hours. The insoluble material was collected by filtration and the filtrate was evaporated under vacuum. The residue was taken up in NaHCO$_3$ (aq) and extracted with CH$_2$Cl$_2$. The combined organic extracts were dried over Na$_2$SO$_4$ and evaporated. The solid was washed with cold Et$_2$O to afford 3',5'-di-O-levulinylnucleosides 2a and 2d.

3',5'-di-O-Levulinylthymidine (2a)

R$_f$(10% MeOH/CH$_2$Cl$_2$): 0.45; Mp: 87–89° C.; IR (KBr): v 3315, 3074, 3006, 2967, 2947, 1743, 1689, and 1660 cm$^{-1}$; $^1$H-NMR (CDCl$_3$, 300 MHz): d 1.88 (s, 3H, Me), 2.14 (s, 3H, Me-Lev), 2.15 (s, 3H, Me-Lev), 2.18 (m, 1H, H$_{2'}$), 2.41 (m, 1H, H$_{2'}$), 2.54 (m, 4H, 2CH$_2$-Lev), 2.73 (m, 4H, 2CH$_2$-Lev), 4.19 (m, 1H, H$_{4'}$), 4.31 (m, 2H, H$_{5'}$), 5.18 (m, 1H, H$_3$), 6.28 (dd, 1H, H$_{1'}$, $^3J_{HH}$8.5, $^3J_{HH}$5.4 Hz), 7.32 (s, 1H, H$_6$), and 9.99 (s, 1H, NH); $^{13}$C-NMR (CDCl$_3$, 75.5 MHz): d 12.3 (Me), 27.48 (CH$_2$-Lev), 27.54 (CH$_2$-Lev), 29.4 (2 Me-Lev), 36.8 (C$_{2'}$), 37.5 (2CH$_2$-Lev), 63.7 (C$_{5'}$), 74.2, 81.8, 84.3 (C$_{1'}$+C$_{3'}$+C$_{4'}$), 111.2 (C$_5$) 134.6 (C$_6$), 150.3 (C$_2$), 163.8 (C$_4$), 171.97 (C=O Lev), 172.02 (C=O Lev), and 206.3 (2C=O Lev); MS (ESI$^+$, m/z): 439 [(M+H)$^+$, 100%], and 461 [(M+Na)$^+$, 50].

3',5'-di-O-Levulinyl-2'-deoxycytidine (2b)

$R_f$ (20% MeOH/CH$_2$Cl$_2$): 0.67; IR (KBr): ν 3390, 2940, 1737, 1715, and 1649 cm$^{-1}$; $^1$H-NMR(MeOH-d$_4$, 200 MHz): d 2.39 (s, 3H, Me-Lev), 2.40 (s, 3H, Me-Lev), 2.43 (m, 1H, H$_{2'}$), 2.75 (m, 1H, H$_{2'}$), 2.79 (m, 4H, 2CH$_2$-Lev), 3.02 (m, 4H, 2CH$_2$-Lev), 4.51 (m, 3H, H$_{4'}$+2H$_{5'}$), 5.46 (m, 1H, H$_{3'}$), 6.17 (d, 1H, H$_5$, $^3J_{HH}$ 7.6 Hz), 6.45 (dd, 1H, H$_{1'}$, $^3J_{HH}$ 8.6, $^3J_{HH}$ 5.7 Hz), and 7.98 (dd, 1H, H$_6$, $^3J_{HH}$ 7.3 Hz); $^{13}$C-NMR (MeOH-d$_4$, 75.5 MHz): d 29.1 (CH$_2$-Lev), 29.2 (CH$_2$-Lev), 29.9 (Me-Lev), 38.9 (2CH$_2$-Lev), 39.2 (C$_{2'}$), 65.5 (C$_{5'}$), 76.5, 84.1, 87.9 (C$_{1'}$+C$_{3'}$+C$_{4'}$), 96.8 (C$_5$), 142.2 (C$_6$), 158.4 (C$_2$), 168.0 (C$_4$), 174.2 (C=O), 174.4 (C=O), and 209.7 (C=O); MS (ESI$^+$, m/z): 446 [(M+Na)$^+$, 70%] and 462 [(M+K)$^+$, 100].

N-Benzoyl-3',5'-di-O-levulinyl-2'-deoxycytidine (2c)

$R_f$ (10% MeOH/CH$_2$Cl$_2$): 0.61; MP: 107–109° C.; IR (KBr): ν 3233, 1744, 1731, and 1668 cm$^{-1}$; $^1$H-NMR (MeOH-d$_4$, 200 MHz): d 2.31 (s, 3H, Me-Lev), 2.38 (s, 3H, Me-Lev), 2.50 (m, 1H, H$_{2'}$), 2.75 (m, 4H, 2CH$_2$-Lev), 2.95 (m, 1H, H$_{2'}$), 3.05 (m, 4H, 2CH$_2$-Lev), 4.59 (m, 3H, H$_{4'}$+2H$_{5'}$), 5.49 (m, 1H, H$_{3'}$), 6.42 (dd, 1H, H$_{1'}$, $^3J_{HH}$ 7.7, $^3J_{HH}$ 5.7 Hz), 7.75 (m, 4H, H$_5$+H$_m$+H$_p$), 8.15 (m, 2H, H$_o$), and 8.45 (d, 1H, H$_6$, $^3J_{HH}$ 7.6 Hz); $^{13}$C-NMR (MeOH-d$_4$, 75.5 MHz): d 29.1 (CH$_2$-Lev), 29.2 (CH$_2$-Lev), 29.9 (Me-Lev), 38.91 (CH$_2$-Lev), 38.94 (CH$_2$-Lev), 39.8 (C$_{2'}$), 65.3 (C$_{5'}$), 76.5, 85.0, 89.3 (C$_{1'}$+C$_{3'}$+C$_{4'}$), 99.0 (C$_5$) 129.5, 130.1 (C$_o$+C$_m$), 134.4 (C$_p$), 135.0 (C$_i$), 146.2 (C$_6$), 158.0 (C$_2$), 165.1 (C$_4$), 169.2 (PhC=O), 174.3 (C=O), 174.4 (C=O), 209.67 (C=O), and 209.72 (C=O); MS (ESI$^+$, m/z): 528 [(M+H)$^+$, 100%], 550 [(M+Na)$^+$, 30], and 566 [(M+K)$^+$, 40].

3',5'-di-O-Levulinyl-2'-deoxyadenosine (2d)

$R_f$ (10% MeOH/CH$_2$Cl$_2$): 0.44; IR (KBr): ν 3418, 3165, 2923, 1738, 1715, and 1644 cm$^{-1}$; $^1$H-NMR (MeOH-d$_4$, 200 MHz): d 2.33 (s, 3H, Me-Lev), 2.39 (s, 3H, Me-Lev), 2.79 (m, 5H, 2CH$_2$-Lev+1H$_{2'}$), 3.00 (m, 4H, 2CH$_2$-Lev), 3.25 (m, 1H, H$_{2'}$), 4.52 (m, 3H, H$_{4'}$+2H$_{5'}$), 5.65 (m, 1H, H$_{3'}$), 6.61 (dd, 1H, H$_{1'}$, $^3J_{HH}$ 6.0, $^3J_{HH}$ 7.9 Hz), 8.41 (s, 1H, H$_2$ or H$_8$), and 8.50 (s, 1H, H$_8$ or H$_2$); $^{13}$C-NMR (MeOH-d$_4$, 75.5 MHz): d 29.1 (CH$_2$-Lev), 29.2 (CH$_2$-Lev), 29.9 (2Me-Lev), 38.1 (C$_{2'}$), 38.9 (2CH$_2$-Lev), 65.2 (C$_{5'}$), 76.5, 84.2, 86.2 (C$_{1'}$+C$_{3'}$+C$_{4'}$), 120.8 (C$_5$) 141.2 (C$_8$), 150.7 (C$_4$), 154.2 (C$_2$), 157.6 (C$_6$), 174.2 (C=O), 174.4 (C=O), 209.68 (C=O), and 209.73 (C=O); MS (ESI$^+$, m/z): 448 [(M+H)$^+$, 20%], 470 [(M+Na)$^+$, 80], and 486 [(M+K)$^+$, 100].

N-Benzoyl-3',5'-di-O-levulinyl-2'-deoxyadenosine (2e)

$R_f$ (10% MeOH/CH$_2$Cl$_2$): 0.71; Mp: 69–71° C.; IR (KBr): ν 3412, 3086, 2958, 1738, 1714, and 1685 cm$^{-1}$; H-NMR (MeOH-d$_4$, 300 MHz): d 2.28 (s, 3H, Me-Lev), 2.35 (s, 3H, Me-Lev), 2.75 (m, 4H, 2CH$_2$-Lev), 2.87 (m, 1H, H$_{2'}$), 2.99 (m, 4H, 2CH$_2$-Lev), 3.30 (m, 1H, H$_{2'}$), 4.52 (m, 3H, H$_{4'}$+2H$_{5'}$), 5.65 (m, 1H, H$_{3'}$), 6.70 (apparent t, 1H, H$_{1'}$, $^3J_{HH}$ 6.8 Hz), 7.75 (m, 3H, 2H$_m$+H$_p$), 8.25 (apparent d, 2H, 2H$_o$, $^3J_{HH}$ 7.4 Hz), 8.75 (s, 1H, H$_2$ or H$_8$), and 8.88 (s, 1H, H$_8$ or H$_2$); $^{13}$C-NMR (MeOH-d$_4$, 75.5 MHz): d 29.0 (CH$_2$-Lev), 29.2 (CH$_2$-Lev), 30.0 (Me-Lev), 37.9 (C$_{2'}$), 38.87 (CH$_2$-Lev), 38.91 (CH$_2$-Lev), 65.2 (C$_{5'}$), 76.4, 84.3, 86.5 (C$_{1'}$+C$_{3'}$+C$_{4'}$), 125.5 (C$_5$) 129.7, 130.0 (C$_o$+C$_m$), 134.1 (C$_p$), 135.1 (C$_i$), 144.5 (C$_8$), 151.3 (C$_4$), 153.3(C$_6$), 153.5 (C$_2$), 168.1 (PhC=O), 174.2 (C=O), 174.3 (C=O), 209.6 (C=O), and 209.7 (C=O); MS (ESI$^+$, m/z): 552 [(M+H)$^+$, 100%] and 574 [(M+Na)$^+$, 17].

3',5'-di-O-Levulinyl-2'-deoxyguanosine (2f)

$R_f$ (20% MeOH/CH$_2$Cl$_2$): 0.65; Mp: 148–150° C.; IR (KBr): ν 3397, 3153, 2940, and 1711 cm$^{-1}$; $^1$H-NMR (DMSO-d$_6$, 200 MHz): d 2.16 (s, 3H, Me-Lev), 2.22 (s, 3H, Me-Lev), 2.60 (m, 5H, 2CH$_2$-Lev+1H$_{2'}$), 2.83 (m, 4H, 2CH$_2$-Lev), 3.00 (m, 1H, H$_{2'}$), 4.29 (m, 3H, H$_{4'}$+2H$_{5'}$), 5.35 (m, 1H, H$_{3'}$), 6.22 (dd, 1H, H$_{1'}$, $^3J_{HH}$ 5.8, $^3J_{HH}$ 8.8 Hz), 6.69 (br s, 2H, NH), and 8.00 (s, 1H, H$_8$); $^{13}$C-NMR (DMSO-d$_6$, 50.3 MHz): d 27.5 (CH$_2$-Lev), 27.7 (CH$_2$-Lev), 29.55 (Me-Lev), 29.60 (Me-Lev), 35.5, 37.4, 37.50 (2CH$_2$-Lev+C$_{2'}$), 63.8 (C$_{5'}$), 74.7, 81.5, 82.6 (C$_{1'}$+C$_{3'}$+C$_{4'}$), 116.8 (C$_5$), 135.1 (C$_8$), 151.2 (C$_4$), 154.0 (C$_2$), 156.9 (C$_6$), 172.1 (C=O), 172.2 (C=O), 206.9 (C=O), and 207.1 (C=O); MS (ESI$^+$, m/z): 464 [(M+H)$^+$, 22%], 486 [(M+Na)$^+$, 75], and 502 [(M+K)$^+$, 100].

N-Isobutyryl-3',5'-di-O-levulinyl-2'-deoxyguanosine (2g)

$R_f$ (20% MeOH/CH$_2$Cl$_2$): 0.85; Mp: 45–47° C.; IR (KBr): ν 3413, 2935, 1740, 1714, 1680, and 1613 cm$^{-1}$; $^1$H-NMR (DMSO-d$_6$, 200 MHz): d 1.23 (d, 6H, Me-$^i$Bu, $^3J_{HH}$ 6.5 Hz), 2.15 (s, 3H, Me-Lev), 2.20 (s, 3H, Me-Lev), 2.55–3.19 (several m, 11H, 4CH$_2$-Lev+2H$_{2'}$+CH-$^i$Bu), 4.32 (m, 3H, H$_{4'}$+2H$_{5'}$), 5.35 (m, 1H, H$_{3'}$), 6.35 (apparent t, 1H, H$_{1'}$, $^3J_{HH}$ 7.2 Hz), 8.35 (s, 1H, H$_8$), 11.80 (br s, 1H, NH), and 12.20 (br s, 1H, NH); $^{13}$C-NMR (DMSO-d$_6$, 50.3 MHz): d 18.86 (Me-$^i$Bu), 18.91 (Me-$^i$Bu), 27.5 (CH$_2$-Lev), 27.6 (CH$_2$-Lev), 29.5 (Me-Lev), 29.6 (Me-Lev), 34.8 (CH-$^i$Bu), 35.5 (C$_{2'}$), 37.38 (CH$_2$-Lev), 37.45 (CH$_2$-Lev), 63.7 (C$_{5'}$), 74.6, 81.7, 82.9 (C$_{1'}$+C$_{3'}$+C$_{4'}$), 120.3 (C$_5$) 137.3 (C$_8$), 148.3, 148.7 (C$_2$+C$_4$), 154.8 (C$_6$), 172.1 (C=O), 172.2 (C=O), 180.2 ($^i$Bu—C=O), 206.9 (C=O), and 207.1 (C=O); MS (ESI$^+$, m/z): 534 [(M+H)$^+$, 100%], 556 [(M+Na)$^+$, 60], and 572 [(M+K)$^+$, 27].

General Procedure for the Enzymatic Hydrolysis of 3',5'-di-O-levulinyl-2'-deoxynucleosides.

To a solution of 2 (0.2 mmol) in 1,4-dioxane (0.35 mL) was added 0.15M phosphate buffer pH=7 (1.65 mL) and the corresponding lipase [ratio of 2:enzyme was 1:1 (w/w) for CAL-A or CAL-B, and 1:3 (w/w) for PSL-C]. The mixture was allowed to react at 250 rpm for the time and at the temperature indicated in Table 1. The reactions were monitored by TLC (10% MeOH/CH$_2$Cl$_2$). The enzyme was filtered off and washed with CH$_2$Cl$_2$, the solvents were distilled under vacuum, and the residue was taken up in NaHCO$_3$ (aq) and extracted with CH$_2$Cl$_2$. The combined organic layers were dried over Na$_2$SO$_4$ and evaporated to give monoacylnucleosides 3 or 4. In case of 3b, the residue was purified by flash chromatography instead of extraction.

3'-O-Levulinylthymidine (3a)

$R_f$ (10% MeOH/CH$_2$Cl$_2$): 0.32; Mp: 50–52° C.; IR (KBr): ν 3449, 3065, 2927, and 1706 cm$^{-1}$; $^1$H-NMR (MeOH-d$_4$, 200 MHz): d 2.09 (d, 3H, Me, J$_{HH}$ 1.3 Hz), 2.39 (s, 3H, Me-Lev.), 2.57 (m, 2H, H$_{2'}$), 2.80 (t, 2H, CH$_2$-Lev, $^3J_{HH}$ 6.0 Hz), 3.05 (t, 2H, CH$_2$-Lev, $^3J_{HH}$ 6.2 Hz), 4.01 (m, 2H, H$_{5'}$), 4.29 (m, 1H, H$_{4'}$), 5.02 (m, 1H, H$_{3'}$), 6.50 (dd, 1H, H$_{1'}$, $^3J_{HH}$ 8.1, $^3J_{HH}$ 6.5 Hz), and 8.04 (d, 1H, H$_6$, J$_{HH}$ 1.3 Hz); $^{13}$C-NMR (CDCl$_3$, 75.5 MHz): d 12.4 (Me), 27.8 (CH$_2$-Lev), 29.6 (Me-Lev), 37.1 (C$_{2'}$), 37.7 (CH$_2$-Lev), 62.2 (C$_{5'}$), 74.9, 85.0, 85.7 (C$_{1'}$+C$_{3'}$+C$_{4'}$), 111.1 (C$_5$)136.5 (C$_6$), 150.6 (C$_2$), 164.3 (C$_4$)172.4 (2C=O Lev), and 206.8 (2C=O Lev); MS (ESI$^+$, m/z): 363 [(M+Na)$^+$, 100%] and 379 [(M+K)$^+$, 30].

3'-O-Levulinyl-2'-deoxycytidine (3b)

$R_f$ (20% MeOH/CH$_2$Cl$_2$): 0.41; $^1$H-NMR (MeOH-d$_4$, 200 MHz): d 2.39 (s, 3H, Me-Lev), 2.47 (m, 1H, H$_{2'}$), 2.67 (m, 1H, H$_{2'}$), 2.75 (m, 2H, CH$_2$-Lev), 3.02 (m, 2H, CH$_2$-Lev), 4.00 (m, 2H, 2H$_{5'}$), 4.30 (m, 1H, H$_{4'}$), 5.49 (m, 1H, H$_{3'}$), 6.15 (d, 1H, H$_5$, $^3J_{HH}$ 6.8 Hz), 6.48 (apparent t, 1H, H$_5$, $^3J_{HH}$ 6.8 Hz), and 8.32 (d, 1H, H$_6$,$^3$ J$_{HH}$ 7.3 Hz); $^{13}$C-NMR (MeOH-d$_4$, 75.5 MHz): d 29.2 (CH$_2$-Lev), 29.9 (Me-Lev), 38.9, 39.5 (C$_{2'}$+CH$_2$-Lev), 63.2 (C$_{5'}$), 76.9, 87.1, 87.8 (C$_{1'}$+C$_{3'}$+C$_{4'}$), 96.6 (C$_5$), 143.0 (C$_6$), 158.2 (C$_2$), 167.6 (C$_4$), 174.2 (C=O), and 209.8 (C=O).

3'-O-Levulinyl-2'-deoxyadenosine (3d)

$R_f$ (20% MeOH/CH$_2$Cl$_2$): 0.66; IR (KBr): ν 3292, 2925, 1730, 1715, 1690, 1644, and 1610 cm$^{-1}$; $^1$H-NMR (MeOH-d$_4$, 200 MHz): d 2.40 (s, 3H, Me-Lev), 2.76 (m, 1H, H$_{2'}$), 2.80 (t, 2H, CH$_2$-Lev, $^3J_{HH}$ 6.2 Hz), 3.05 (t, 2H, CH$_2$-Lev, $^3J_{HH}$ 6.2 Hz), 3.14 (m, 1H, H$_{2'}$), 4.04 (m, 2H, 2H$_{5'}$), 4.40 (m, 1H, H$_{4'}$), 5.66 (d, 1H, H$_3$, $^3J_{HH}$ 6.0 Hz), 6.61 (dd, 1H, H$_{1'}$, $^3J_{HH}$ 5.7, $^3J_{HH}$ 9.1 Hz), 8.39 (s, 1H, H$_2$ or H$_8$), and 8.50 (s, 1H, H$_8$ or H$_2$); $^{13}$C-NMR (MeOH-d$_4$, 75.5 MHz): d 29.1 (CH$_2$-Lev), 29.9 (Me-Lev), 38.9, 39.0 (C$_{2'}$+CH$_2$-Lev), 64.0 (C$_{5'}$), 77.5, 87.6, 87.9 (C$_{1'}$+C$_{3'}$+C$_{4'}$), 121.2 (C$_5$)141.9 (C$_8$), 150.1 (C$_4$), 153.8 (C$_2$), 157.8 (C$_6$), 174.3 (C=O), and 209.8 (C=O); MS (ESI$^+$, m/z): 350 [(M+H)$^+$, 100%], 372 [(M+Na)$^+$, 100], and 388 [(M+K)$^+$, 60].

N-Isobutyryl-3'-O-levulinyl-2'-deoxyguanosine (3g)

$R_f$ (20% MeOH/CH$_2$Cl$_2$): 0.75; Mp: 170–172° C.; IR (KBr): ν 3415, 2961, 2929, 2859, 1725, 1686, and 1614 cm$^{-1}$; $^1$H-NMR (MeOH-d$_4$, 200 MHz): d 1.41 (d, 6H, Me—$^i$Bu, $^3J_{HH}$ 6.8 Hz), 2.38 (s, 3H, Me-Lev), 2.70–3.09 (m, 7H, 2CH$_2$-Lev+2H$_{2'}$+CH—$^i$Bu), 3.98 (d, 2H, 2H$_{5'}$, $^3J_{HH}$ 3.4 Hz), 4.45 (m, 1H, H$_{4'}$), 5.60 (m, 1H, H$_{3'}$), 6.51 (dd, 1H, H$_{1'}$, $^3J_{HH}$ 5.9, $^3J_{HH}$ 8.4 Hz), and 8.45 (s, 1H, H$_8$); $^{13}$C-NMR (MeOH-d$_4$, 50.3 MHz): d 19.6 (Me—$^i$Bu), 29.2 (CH$_2$-Lev), 30.0 (Me-Lev), 37.2 (CH—$^1$Bu), 38.9, 39.3 (C$_{2'}$+CH$_2$-Lev), 63.3 (C$_{5'}$), 76.8, 85.8, 87.3 (C$_{1'}$+C$_{3'}$+C$_{4'}$), 121.5 (C$_5$), 139.7 (C$_8$), 150.0, 150.5 (C$_2$+C$_4$), 157.6 (C$_6$), 174.2 (C=O), 182.0 ($^1$Bu—C=O), and 209.7 (C=O); MS (ESI$^+$, m/z): 436 [(M+H)$^+$, 15%] and 458 [(M+Na)$^+$, 50].

5'-O-Levulinylthymidine (4a)

$R_f$ (10% MeOH/CH$_2$Cl$_2$): 0.22; Mp: 141–143° C.; IR (KBr): ν 3393, 3215, 2934, 1737, 1724, 1643, and 1629 cm$^{-1}$; $^1$H-NMR (DMSO-d$_6$, 200 MHz): d 1.91 (s, 3H, Me), 2.27 (s, 3H, Me-Lev.), 2.30 (m, 2H, H$_{2'}$), 2.66 (m, 2H, CH$_2$-Lev), 2.89 (t, 2H, CH$_2$-Lev, $^3J_{HH}$ 6.2 Hz), 4.07 (m, 1H, H$_{4'}$), 4.35 (m, 3H, H$_{3'}$+2H$_{5'}$), 5.55 (d, 1H, OH), 6.32 (t, 1H, H$_{1'}$, $^3J_{HH}$ 7.0 Hz), 7.6 (s, 1H, H$_{6'}$), and 11.45 (s, 1H, NH); $^{13}$C-NMR (DMSO-d$_6$, 50.3 MHz): d 12.02 (Me), 27.4 (CH$_2$-Lev), 29.4 (Me-Lev), 37.2 (C$_{2'}$), 38.4 (CH$_2$-Lev), 63.8 (C$_{5'}$), 70.1 (C$_{3'}$), 83.5, 83.6 (C$_{1'}$+C$_{4'}$), 109.7 (C$_5$), 135.7 (C$_6$), 150.3 (C$_4$), 163.6 (C$_2$), 172.1 (C=O Lev), and 206.7 (C=O Lev); MS (ESI$^+$, m/z): 341 [(M+H)$^+$, 40%], 379 [(M+Na)$^+$, 100], and 379 [(M+K)$^+$, 80].

N-Benzoyl-5'-O-levulinyl-2'-deoxycytidine (4c)

$R_f$ (10% MeOH/CH$_2$Cl$_2$): 0.37; Mp: 50–52° C. IR (KBr): ν 3410, 2919, 1738, 1701, and 1650 cm$^{-1}$; $^1$H-NMR (CDCl$_3$, 300 MHz): d 2.20 (s, 3H, Me-Lev), 2.25 (m, 1H, H$_{2'}$), 2.58 (m, 2H, CH$_2$-Lev), 2.75 (m, 1H, H$_{2'}$), 2.82 (m, 2H, CH$_2$-Lev), 3.35 (s, 1H, OH), 4.25 (m, 1H, H$_{3'}$), 4.40 (m, 3H, 2H$_{5'}$+H$_{4'}$), 6.30 (apparent t, 1H, H$_{1'}$, $^3J_{HH}$ 6.2 Hz), 7.55 (m, 4H, H$_5$+2H$_m$+H$_p$), 7.90 (apparent d, 2H, H$_o$, $^3J_{HH}$ 7.1 Hz), 8.20 (d, 1H, H$_6$,$^3J_{HH}$ 7.4 Hz), and 8.78 (s, 1H, NH); $^{13}$C-NMR (CDCl$_3$, 50.3 MHz): d 27.7 (CH$_2$-Lev), 29.6 (Me-Lev), 37.7 (CH$_2$-Lev), 41.3 (C$_{2'}$), 63.7 (C$_{5'}$), 70.6, 84.8, 87.4 (C$_{1'}$+C$_{3'}$+C$_{4'}$), 96.8 (C$_5$), 127.6, 128.7 (C$_o$+C$_m$), 132.8 (C$_i$), 133.0 (C$_p$), 144.2 (C$_6$), 155.1 (C$_2$), 162.4 (C$_4$), 166.7 (PhC=O), 172.6 (C=O), and 206.8 (C=O); MS (ESI$^+$, m/z): 430 [(M+H)$^+$, 20%], 452 [(M+Na)$^+$, 65], and 468 [(M+K)$^+$, 40].

N-Benzoyl-5'-O-levulinyl-2'-deoxyadenosine (4e)

$R_f$ (10% MeOH/CH$_2$Cl$_2$): 0.50; Mp: 69–71° C.; IR (KBr): ν 3413, 2959, 2928, 1726, 1637, and 1616 cm$^{-1}$; H-NMR (MeOH-d$_4$, 300 MHz): d 2.30 (s, 3H, Me-Lev), 2.70 (m, 3H, CH$_2$-Lev+1H$_{2'}$), 2.92 (m, 2H, CH$_2$-Lev), 3.15 (m, 1H, H$_{2'}$), 4.40 (m, 1H, H$_{4'}$), 4.52 (m, 2H, 2H$_{5'}$), 4.85 (m, 1H, H$_{3'}$), 6.75 (apparent t, 1H, H$_{1'}$, $^3J_{HH}$6.2 Hz), 7.80 (m, 3H, 2H$_m$+H$_p$), 8.30 (m, 2H, 2H$_o$), 8.78 (s, 1H, H$_2$ or H$_8$), and 8.92 (s, 1H, H$_8$ or H$_2$), $^{13}$C-NMR (MeOH-d$_4$, 75.5 MHz): d 29.0 (CH$_2$-Lev), 29.9 (Me-Lev), 38.9, 40.8 (CH$_2$-Lev+C$_{2'}$), 65.3 (C$_{5'}$), 72.6, 86.51, 86.54 (C$_{1'}$+C$_{3'}$+C$_{4'}$), 125.7 (C$_5$), 129.7, 130.0 (C$_o$+C$_m$), 134.2(C$_p$), 135.2 (C$_i$), 144.6 (C$_8$), 151.4 (C$_4$), 153.3(C$_6$), 153.5 (C$_2$), 168.4 (PhC=O), 174.5 (C=O), and 209.7 (C=O); MS (ESI$^+$, m/z): 476 [(M+Na)$^+$, 100%] and 492 [(M+K)$^+$, 53].

N-Isobutyryl-3'-O-levulinyl-2'-deoxyguanosine (4g)

$R_f$ (20% MeOH/CH$_2$Cl$_2$): 0.60; Mp: 45–47° C.; IR(KBr): ν 3415, 2930, 1720, and 1685 cm$^{-1}$; $^1$H-NMR(MeOH-d$_4$, 200 (MHz): d 1.41 (d, 6H, Me—$^i$Bu, $^3J_{HH}$ 6.8 Hz), 2.33 (s, 3H, Me-Lev), 2.59–3.07 (m, 7H, 2CH$_2$-Lev+2H$_{2'}$+CH—$^i$Bu), 4.32 (m, 1H, H$_{4'}$), 4.50 (m, 2H, H$_{5'}$), 4.75 (m, 1H, H$_{3'}$), 6.50 (apparent t, 1H, H$_{1'}$, $^3J_{HH}$ 6.4 Hz), and 8.32 (s, 1H, H$_8$); $^{13}$C-NMR (MeOH-d$_4$, 75.5 MHz): d 19.7 (Me—$^i$Bu), 29.0 (CH$_2$-Lev), 29.9 (Me-Lev), 37.2 (CH—$^i$Bu), 38.9, 41.1 (C$_{2'}$+CH$_2$-Lev), 65.3 (C$_{5'}$), 72.6, 86.1, 86.5 (C$_{1'}$+C$_{3'}$+C$_{4'}$), 121.8 (C$_5$) 139.8 (C$_8$), 150.0, 150.5 (C$_2$+C$_4$), 157.8 (C$_6$), 174.5 (C=O), 182.0 ($^i$Bu—C=O), and 209.7 (C=O); MS (ESI$^+$, m/z): 436 [(M+H)$^+$, 20%], 458 [(M+Na)$^+$, 100], and 474 [(M+K)$^+$, 50].

General Procedure for the Enzymatic Hydrolysis of Thymidine Tetramer Bearing Levulinyl Protecting Groups at Each of the 3',-O and 5'-O Terminal Positions To a solution of diprotected tetramer in 1,4-dioxane is added 0.15M phosphate buffer pH=7 and the corresponding lipase [ratio of tetramer:enzyme is 1:1 (w/w) for CAL-A or CAL-B, and 1:3 (w/w) for PSL-C]. The mixture is allowed to react at 250 rpm for 62 h at 40°. The reactions are monitored by TLC (10% MeOH/CH$_2$Cl$_2$). The enzyme is filtered off and washed with CH$_2$Cl$_2$, the solvents are distilled under vacuum, and the residue is taken up in NaHCO$_3$ (aq) and extracted with CH$_2$Cl$_2$. The combined organic layers are dried over Na$_2$SO$_4$ and evaporated to give monoacylpolynucleotides.

What is claimed is:

1. A method for the selective deprotection of a 3',5'-di-O-levulinyl nucleoside comprising selecting a lipase effective to direct regioselective hydrolysis of one of said levulinyl positions of the nucleoside; and contacting the 3',5'-di-O-levulinyl nucleoside with said lipase for a time and under conditions effective to yield the corresponding 3'-O-levulinyl or 5'-O-levulinyl nucleoside.

2. The method of claim 1 wherein said lipase is CAL-A, CAL-B, PSL-C, porcine pancreatic lipase, *Chromobacteriaum viscosum* lipase, *Mucor miehei* lipase, *Humicola lanuginosa* lipase, *Penicillium camemberti* lipase, or *Candida rugosa* lipase.

3. The method of claim 2 wherein said lipase is CAL-A.
4. The method of claim 2 wherein said lipase is CAL-B.
5. The method of claim 2 wherein said lipase is PSL-C.

6. A method for the selective deprotection of a 3',5'-di-O-levulinyl nucleoside at the 5'-O-levulinyl position comprising selecting a lipase effective to direct regioselective hydrolysis of said 3',5'-di-O-levulinyl nucleoside at the 5'-O-levulinyl position and contacting said 3',5'-di-O-levulinyl nucleoside with said lipase for a time and under conditions effective to yield a 3'-O-levulinyl nucleoside.

7. The method of claim 6 wherein said lipase is CAL-B.

8. A method for the selective deprotection of a 3',5'-di-O-levulinyl nucleoside at the 3'-O-levulinyl position comprising selecting a lipase effective to direct regioselective hydrolysis of said 3',5'-di-O-levulinyl nucleoside at the 3'-O-levulinyl position and contacting said 3',5'-di-O-levulinyl nucleoside with said lipase for a time and under conditions effective to yield a 5'-O-levulinyl nucleoside.

9. The method of claim 8 wherein said lipase is CAL-A.

10. The method of claim 8 wherein said lipase is PSL-C.

11. A method for the selective deprotection of a 3',5'-di-O-levulinyl nucleoside at the 5'-O-levulinyl position comprising selecting a lipase effective to direct regioselective hydrolysis of said 3',5'-di-O-levulinyl nucleoside at the 5'-O-levulinyl position and contacting said 3',5'-di-O-levulinyl nucleoside with said lipase for a time and under conditions effective to yield a 3'-O-levulinyl nucleoside wherein said 3',5'-di-O-levulinyl nucleoside has one of the following formulas:

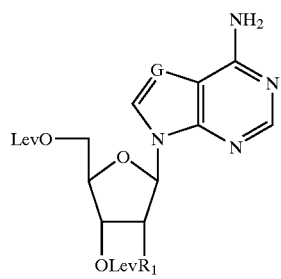

I

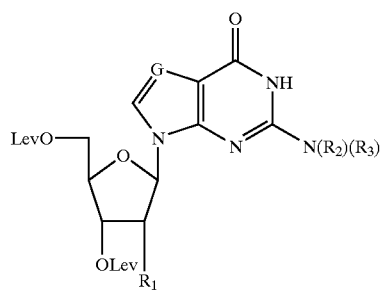

II

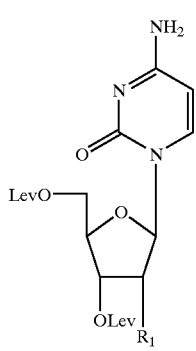

III

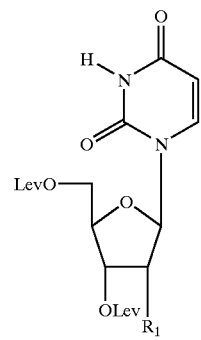

IV

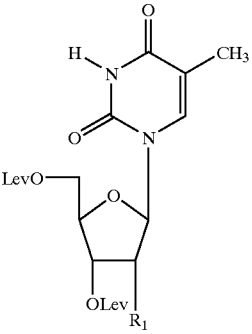

V wherein:

$R_1$ is —H, -hydroxyl, a protected hydroxyl, or a 2'-substituent; and $R_2$ and $R_3$ are, independently, —H or an amino protecting group;

G is N or CH; and

Lev is —C(O)—(CH$_2$)$_2$—C(O)—CH$_3$.

12. The method of claim 11 wherein said lipase is CAL-B.

13. The method of claim 12 wherein said 3',5'-di-O-levulinyl nucleoside is an adenosine, cytosine, thymidine, or an N-isobutyl guanosine.

14. A method for the selective deprotection of a 3',5'-di-O-levulinyl nucleoside at the 3'-O-levulinyl position comprising selecting a lipase effective to direct regioselective hydrolysis of said 3',5'-di-O-levulinyl nucleoside at the 3'-O-levulinyl position and contacting said 3',5'-di-O-levulinyl nucleoside with said lipase for a time and under conditions effective to yield a 5'-O-levulinyl nucleoside wherein said 3',5'-di-O-levulinyl nucleoside has one of the following formulas:

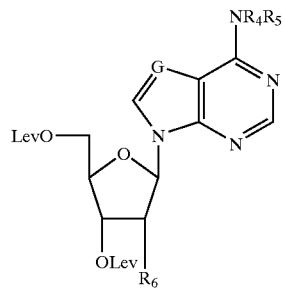

VI

-continued

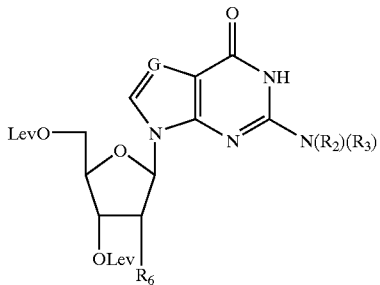
VII

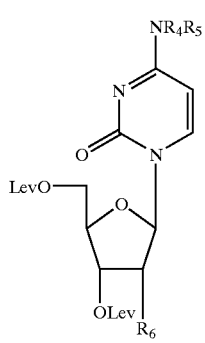
VIII

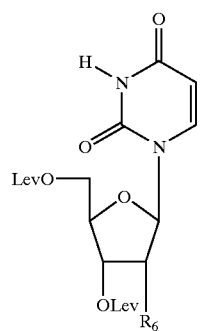
IX

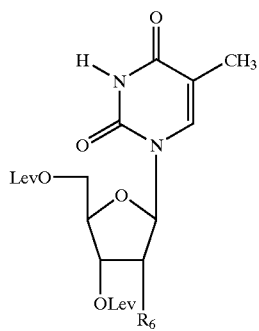
X wherein:

R$_6$ is —H, or —OH;

R$_2$, R$_3$, R$_4$, and R$_5$ are each, independently, —H or an amino protecting group;

G is N or CH; and

Lev is —C(O)—(CH$_2$)$_2$—C(O)—CH$_3$.

15. The method of claim 14 wherein said lipase is CAL-A.

16. The method of claim 14 wherein said lipase is PSL-C.

17. The method of claim 15 wherein said 3',5'-di-O-levulinyl nucleoside is 3',5'-di-O-levulinyl thymidine, 3',5'-di-O-levulinyl cytosine, or 3',5'-di-O-levulinyl N-benzoyl adenosine.

18. The method of claim 16 wherein said 3',5'-di-O-levulinyl nucleoside is N-isobutylguanosine.

19. A method for the selective deprotection of a 3',5'-di-O-levulinyl nucleoside at the 5'-O levulinyl position wherein said 3',5'-di-O-levulinyl nucleoside has one of the following formulas:

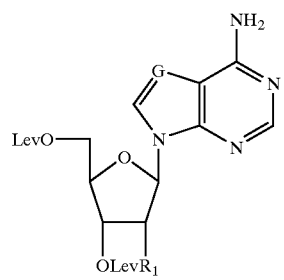
I

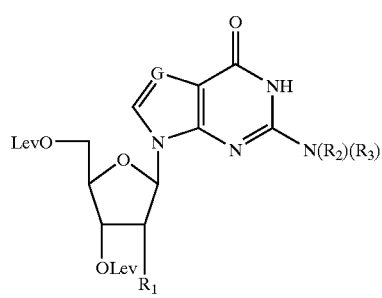
II

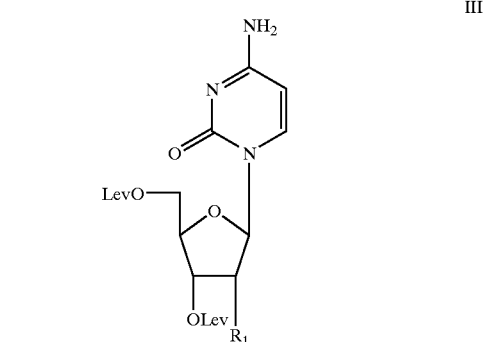
III

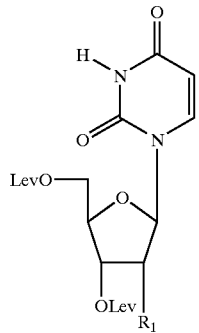
IV

V

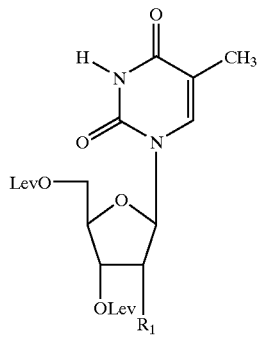

wherein:

R₁ is —H, -hydroxyl, a protected hydroxyl, or a 2'-substituent; and

R₂ and R₃ are, independently, —H or an amino protecting group;

G is N or CH; and

Lev is —C(O)—(CH₂)₂—C(O)—CH₃;

comprising contacting said 3',5'-di-O-levulinyl nucleoside with CAL-B for a time and under conditions effective to hydrolyze said 3',5'-di-O-levulinyl nucleoside at the 5'-O-levulinyl position.

20. The method of claim 19 wherein said 3'-,5'-di-O-levulinylnucleoside comprises an adenosine, cytosine, thymidine, or an N-isobutyl guanosine moiety.

21. A method for the selective deprotection of a 3',5'-di-O-levulinyl nucleoside at the 3'-O-levulinyl position wherein said 3',5'-di-O-levulinyl nucleoside has one of the following formulas:

VI

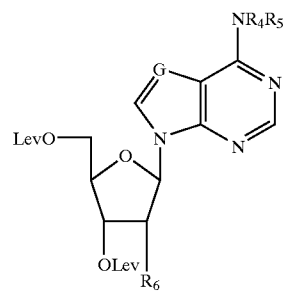

VII

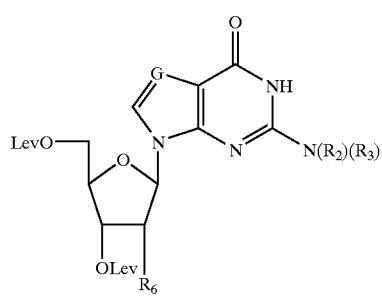

VIII

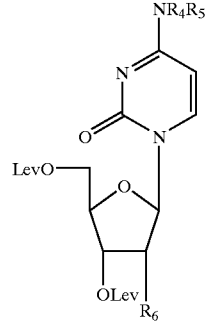

IX

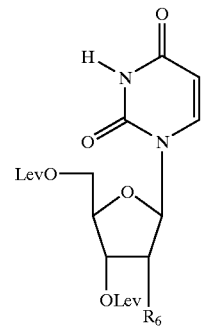

X

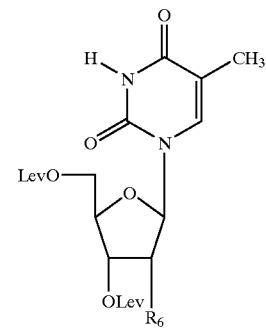

wherein:

R₆ is —H or -hydroxyl;

R₂, R₃, R₄, and R₅ are each, independently, —H or an amino protecting group;

G is N or CH; and

Lev is —C(O)—(CH₂)₂—C(O)—CH₃;

comprising contacting said 3',5'-di-O-levulinyl nucleoside with PSL-C for a time and under conditions effective to hydrolyze said 3',5'-di-O-levulinyl nucleoside at the 3'-O-levulinyl position.

22. The method of claim 20 wherein said 3'-,5'-di-O-levulinyl nucleoside comprises an N-isobutylguanosine moiety.

23. A method for the selective deprotection of a 3',5'-di-O-levulinyl nucleoside at the 3'-O-levulinyl position wherein 3',5'-di-O-levulinyl nucleoside has one of the following formulas:

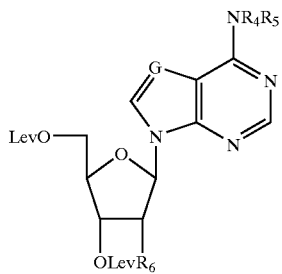

VI

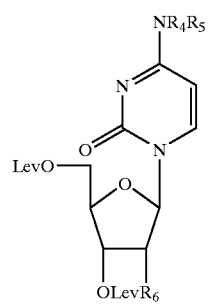

VIII

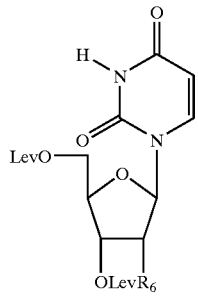

IX

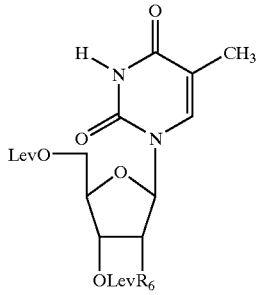

X wherein:

$R_6$ is —H, or —OH;

$R_2$, $R_3$, $R_4$, and $R_5$ are each, independently, —H or an amino protecting group;

G is N or CH; and

Lev is —C(O)—(CH$_2$)$_2$—C(O)—CH$_3$.

comprising contacting said 3′,5′-di-O-levulinyl nucleoside with PSL-C for a time and under conditions effective to hydrolyze said 3′,5′-di-O-levulinyl nucleoside at the 3′-O-levulinyl position.

24. The method of claim 20 wherein said 3′-,5′-di-O-levulinyl nucleoside comprises a thymidine, cytosine, or N-benzoyl adenosine moiety.

* * * * *